United States Patent [19]

Collange et al.

[11] Patent Number: 4,490,221
[45] Date of Patent: Dec. 25, 1984

[54] PROCESS FOR PREPARING IODOTHYRONINES AND IODOTHYROACETIC ACIDS BY ELECTROCHEMICAL REDUCTION AT CONTROLLED POTENTIAL

[75] Inventors: Edmond Collange, Longvic; Michel Pâris; Nicole Autissier, both of Dijon, all of France

[73] Assignee: Spiral Societe a Responsabilite Limitee dite, France

[21] Appl. No.: 489,536

[22] Filed: Apr. 28, 1983

[30] Foreign Application Priority Data

Apr. 30, 1982 [FR] France ................................ 82 07590

[51] Int. Cl.³ .................... C25B 3/00; C07C 101/72
[52] U.S. Cl. .................................. 204/72; 204/59 R; 204/73 R
[58] Field of Search ...................... 204/72, 59 R, 73 R

[56] References Cited

PUBLICATIONS

Synthesis of Thyroid Hormone Metabolites by Photolysis of Thyroxine and Thyroxine Analogs in the Near UV, pp. 1492–1496, Mar. 1982, vol. 79, Walt and Cahumann, Proc. Natl. Acad. Sci., USA.
Synthesis of $^{125}$I-reverse $T_3$ using a low and a high 3,3'-di-iodothyronine/$^{125}$I ratio, pp. 773–776, vol. 41 (8), 1981, Scandinavian Jour. Clinical and Lab. Investigation.
Preparation of High Specific Activity Labelled 3,3',5'--Triiodothyronine Reverse T-3, pp. 174–176, vol. 5 (4–5) 1978, International Journal of Nuclear Medicine and Biology.
Saishin Igaku, vol. 31 (5), 1976, pp. 893–897.

Primary Examiner—T. Tung
Assistant Examiner—Nathan Thane
Attorney, Agent, or Firm—Harpman & Harpman

[57] ABSTRACT

The invention relates to a process for preparing triiodo-, di-iodo- and mono-iodothyronines and tri-iodo, di-iodo and mono-iodothyroacetic acids, respectively from thyronine, triiodo or diiodothyro- nine and tetra-, tri- or diiodothyroacetic acid, by electrochemical reduction at controlled potential, in an aqueous medium rendered alkaline by the addition in particular of a tetraalkylammonium hydroxide, whereby either the iodine in 5 position or the iodine in 3 position is selectively reduced, depending on the potential at which operation is carried out, and which is determined previously by plotting a polarograph of the starting substance.

16 Claims, 6 Drawing Figures

PROCESS FOR PREPARING IODOTHYRONINES AND IODOTHYROACETIC ACIDS BY ELECTROCHEMICAL REDUCTION AT CONTROLLED POTENTIAL

The invention relates to a process for synthesizing iodothyronines and iodothyroacetic acids by selective elimination of one or two atoms of iodine by electrolytic reduction at controlled potential.

3,3',5'-L-triiodothyronine (reverse $T_3$ or $rT_3$) is one of the four iodothyronines secreted by the thyroid normally found in the blood, the other three being thyroxine or 3,5,3',5'-L-tetraiodothyronine ($T_4$), 3,5,3'-L-triiodothyronine ($T_3$) and 3,3'-L-diiodothyronine (reverse $T_2$ or $rT_2$). The formulae of the iodothyronines are shown in Table I hereinafter. Due to the highly sensitive radioimmunological techniques, the concentration of $rT_3$ in plasma has been determined (CHOPRA I. J.—J. Clin. Invest., 1974, 54, 583). It is of the order of 20 to 30 ng/100 ml whilst that of $T_3$ is on average 120 ng/100 ml and that of $T_4$ from 6 to 8 µg/100 ml. The plasma concentration of $rT_2$ would be less than 1 ng/100 ml. (Meinhold H. and Shurnbrand P.—J. Clin. Chem. Clin. Biochem., 1977, 15, 419).

Contrary to $T_4$ and especially to $T_3$ which is about five times more active than $T_4$, $rT_3$, like $rT_2$, has no metabolic activity; on the other hand, $rT_3$ is weakly inhibitory of the thyroid concentration of the $I^-$ ions (BARKER S. B. et col.—Ann. N.Y. Acad. Sci., 1960, 82, 545. COURRIER R., et col.—Bull. Soc. Chim. Biol., 1955, 37, 439, ROCHE J., et col.—C.R. Soc. Biol., 1958, 152, 1067).

The endocrine secretion of the thyroid body has been considered for a long time as the sole source of iodothyronines. At the present time, it is admitted that the major part of circulating $T_3$, $rT_3$ and $rT_2$ is of cellular origin. $T_3$ and $rT_3$ come from the deiodization of $T_4$ respectively in 5' and in 5. As for $rT_2$, it appears to be produced from $rT_3$ rather than from $T_3$ or $T_4$ at the expense of which it nevertheless forms in small quantities. A role of prehormone has thus very often developed to $T_4$.

Iodothyroacetic acids are thyroid metabolites which come from the corresponding iodothyronines, which undergo at tissue and principally at liver and kidney level, a degradation of the alanine chain by oxidation, probably after passage in the form of iodothyropyruvic acids. The formulae of the iodothyroacetic acids are shown in Table II hereinafter. Only the 3,5,3',5'-tetraiodothyroacetic acids (or TETRAC) and the 3,5,3'-triiodothyroacetic acid (or TRIAC) have been demonstrated with certainty in the organism (J. ROCHE, R. MICHEL, P. JOUAN and W. WOLF—C.R. Acad. Sci. 1953 241 1880, J. ROCHE, R. MICHEL, P. JOUAN and W. WOLF—Endocrinology 1956 59 425, J. ROCHE and R. MICHEL—Ann. N.Y. Acad. Sci. 1960 86 454). Traces of TETRAC have been found in the blood near the thyroid hormones, and it has been shown that its concentration decreases in the course of fasting (A. VAGENAKIS, A. BURGER, J. I. PORTNAY, etc.—J. Clin. Endocri. Metab. 1975 41 191) and increases after administration of amiodarone (A. BURGER cited by J. ROCHE and R. MICHEL—Ann. Endocr. (Paris) 1977 38 243).

As for the other iodothyroacetic acids, particularly the 3,3',5'-triiodothyroacetic (or rTRIAC) and 3,3'-diiodothyroacetic (or rDIAC) acids, although their presence in the organism has not yet been demonstrated, it may nonetheless be thought that they are hormonal metabolites since the corresponding iodothyronines $rT_3$ and $rT_2$ are compounds normally present in the organism.

Studies on the biological activity of TETRAC and of TRIAC have shown that their properties were only slightly different from those of the iodothyronines from which they derive. The intensity of the responses on various tests of thyroid activity nevertheless indicate that their action is inferior to that of their precursors. However, they prove to be elective lipolytics, particularly at cholesterol level (R. MICHEL, F. CABANNE, R. TRUCHOT and H. TRONLOISEL—C.R. Sci. Biol. 1957 151 479—Bull. Soc. Chim. Biol. 1958 40 1241). The TRIAC has thus retained the attention of clinicians who still use this product at the present time in the treatment of obesity where it proves to be particularly advantageous in reducing excess weight.

The fact of having sufficient quantities of $rT_3$ at a reasonable price is interesting in two respects:
- on the one hand, a clinical interest of the dosage of $rT_3$, in the immediate future;
- on the other hand, a therapeutic interest as antithyroid drug over a longer term.

The clinical interest of the dosage of $rT_3$ results especially from the fact that the variations in the plasma levels of $rT_3$ and of $T_3$ are almost always in reverse direction, which translates a certain compensation of the peripheral formation of $T_3$ by $rT_3$ (and vice versa) and consequently the possibility of a physiological balance between the two processes of deiodization of $T_4$ and that of the rupture of this balance. Consequently, from the biological standpoint, the dosage of $rT_3$ associated with that of total $T_3$, even of total $T_4$ may furnish a certain amount of information. In this way, an increase in the serum concentraton of $rT_3$ accompanied by a decrease in the level of $T_3$ is observed:
- in new-born babies and the elderly;
- under the effect of certain drugs such as amiodarone, propanolol, dexamethasone and certain synthetic antithyroid drugs, such as benzylthiouracile;
- in the course of fasting, the excess of glucides producing the reverse phenomenon;
- in various acute or subacute pathological states, such as hepatic cirrhoses, renal disorders, certain febrile states.

The assay of $rT_3$ in the blood therefore presents an interest:
- to follow the thyroid state of a patient who, in addition to his thyroid disorder, presents other disorders of the type as indicated above or when he receives certain drugs. A study of the variations of the rate of $rT_3$ in the blood seems to have to constitute a good index of the effectiveness of the benzylthiouracile, synthetic antithyroid drug, and especially to enable the use of this product to be better monitored, the concentration of $rT_3$ being increased considerably in the course of treatment;
- in the diagnosis of certain hyperthyroidisms—$T_3$-thyrotoxicoses—characterized by an increase in the serum level of $T_3$ and $rT_3$ with a more or less marked hypothyroxinaemia;
- in the course of slimming cures. The obese patients often present a slight hypothyroidism, characterized by a significant drop in the serum concentration of $T_3$ (not published). The establishment of a low-calorie diet brings about both a reduction in the serum level of $T_3$ and an increase in that of $rT_3$. The simultaneous dosage of $T_4$, $T_3$ and $rT_3$ in the course of the cure gives information on the development of the treatment and therefore enables the effects thereof on the thyroid activity of the patients to be monitored.

In addition, the determination of the content in $rT_3$ of the human amniotic liquid has shown that said content is about 300 ng/100 ml between the 15th and 30th week of pregnancy and becomes close to 100 ng/ml from the 31st to 42nd week. An excess of $rT_3$ is the sign of a deviation of the metabolism of $T_4$.

The assay of $rT_3$ in the amniotic liquid is therefore capable of allowing early detection of hypothyroidism of certain new-born babies which must, as is known, be treated very quickly after birth.

The therapeutic interest of $rT_3$ results from the examination of still fragmentary works on the biological activity of this hormone (ROCHE J., et col.—Bull. Soc. Chim. (France), 1957, 462 and Bull. Soc. Chim. (France), 1979, 715), COIRO V., et col.—Endocrinology, 1980, 106, 68) which lead one to think that $rT_3$ may reduce the metabolic activities of $T_3$. It therefore appears that $rT_3$ might be used in the treatment of hyperthyroidisms characterized by an abnormally high secretion of $T_4$ and $T_3$.

The possibility of having sufficient quantities of $rT_3$ at a moderate cost price incontestably presents a considerable interest both in the field of research for a thorough study of the biological effects of this substance and in the industrial field for developing a product capable of being used in clinical analysis or in therapeutics.

Examination of the earlier works on the synthesis of $rT_3$

The team of ROCHE and MICHEL (cf. above) is the first to have proposed methods of snythesis of various thyronines iodized by iodization or by deiodization of various derivatives; certain were then taken up again and slightly amended (VARCOE J. S. and WARBURTON W. K.—J. Chem. Soc., 1960, 2711). All these methods bear on the difference in reactivity of the two phenyl cycles A and B of thyronine of formula:

It has been clearly shown (ROCHE J., et col.—Bull. Soc. Chim. (France), 1957, 462 and Bull. Soc. Chim. (France) 1959, 715) that the phenol group A considerably increased the reactivity of the positions 3' and 5' during iodization of the thyronine; on the contrary, the positions 3 and 5 of the cycle B remain inaccessible, and the synthesis of thyroxine can be effected, for example, only by iodization of the 3,5-diiodothyronine or $T_2$, itself obtained by condensation by oxidation of diiodotyrosine (HARINGTON C. R. and PITT-RIVERS R. V.—Biochem. J., 1945, 39, 157; PITT-RIVERS R. V.—Biochem. J., 1948, 43, 223; PITT-RIVERS R. V. and JAMES A. J.—Biochem. J., 1958, 70, 173).

Although synthesis of the thyroxine does not pose any major problem concerning the purity of the compound obtained, it is a different matter when it is desired to prepare a mono-, di- or tri-iodized thyronine, as the existing methods always leave a doubt on the purity of the isolated iodothyronines; these may in fact be soiled by the compound more or less rich in iodine. Moreover, present methods of analysis do not enable low rates of impurity to be metered with sufficient accuracy.

In the particular case of $rT_3$, it is imperative that there be no doubt as to its purity since it is desired to assess its hormonal activity with certainty; the least trace of $T_4$, and especially of $T_3$ whose metabolic action is about five times greater than that of $T_4$, inevitably leads to manifest errors in interpretation on the actual activities of these products. It is for this reason that iodization of the 3-iodothyronine is not satisfactory as $rT_3$ may be soiled by 3,3'-diiodothyronine or $rT_2$; in the same way, selective hydrogenation of the thyroxine (VARCOE J. S. and WARBURTON W. K.—J. Chem. Soc., 1960, 2711) may lead to $rT_3$ containing $T_4$ and 3',5'-diiodothyronine or $T'_2$. At present, the only valid method is that of (SHIBA R. and CAHNMANN H. J.—J. Org. Chem., 1964, 29, 1952) who condense with a yield of only 20% the 4-hydroxy-3-iodophenylpyruvic acid (DIHPPA) with diiodotyrosine (DIT).

It is an object of the present invention to provide a new process for synthesis of the tri-iodo, di-iodo and mono-iodo-thyronines, and similarly of tri-iodo-, di-iodo and mono-iodo-thyroacetic acids respectively from thyroxine, tri-iodo- and di-iodo-thyronines, and tetra-iodo, tri-iodo and di-iodo-thyroacetic acids, by selective electrochemical reduction at controlled potential, in an aqueous medium rendered alkaline by the addition of sodium hydroxide, or preferably a tetraalkylammonium hydroxide.

According to the potential at which operation is carried out, either the iodine in 5 position or the iodine in 3 position, is selectively eliminated, or both at the same time.

It is a particular object of the invention to provide a process for preparing a highly pure $rT_3$, by electrochemical reduction at controlled potential of the thyroxine.

The purity of the product obtained, determined by a new method of polarographic analysis, is greater than a rate of impurity of $0.5°/··$ (mol for mol) and the yield of $rT_3$ with respect to the starting thyroxine is quantitative.

BRIEF DESCRIPTION OF THE DRAWINGS

FIG. 6 shows the polarographs of the reduction product obtained (a) and of the TETRAC (b).

PRINCIPLE OF THE PROCESS OF ELECTROCHEMICAL REDUCTION ACCORDING TO THE INVENTION

In an aqueous medium rendered alkaline by the addition of sodium hydroxide or, preferably, a tetraalkylammonium hydroxide, the thyroxine and the various iodothyronines studied are reduced by successive stages at different potentials.

Figure 1:
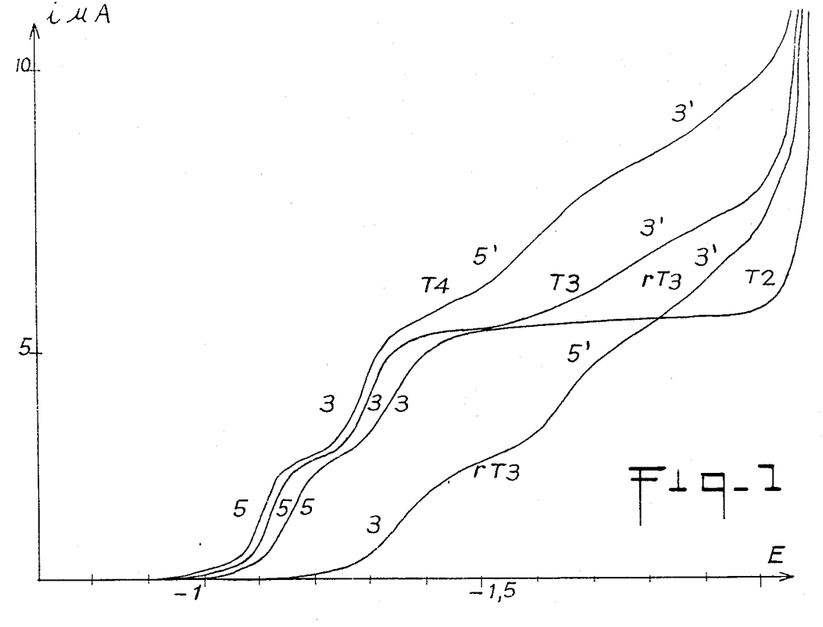
FIG. 1 shows the polarographs of $T_4$, $T_3$, $rT_3$, and $T_2$ in aqueous solution at the concentration of $5.10^{-4}M$, in tetramethylammonium hydroxide (0.1M).

FIG. 1 shows the polarographs of $T_4$, $T_3$, $rT_3$ and $T_2$ in aqueous solution at the concentration of $5.10^{-4}M$, in tetramethylammonium hydroxide (0.1M). By comparing these polarographs, it is seen that each wave can be attributed to the reduction of an iodine in a determined position.

In pulsed polarography, this reduction by stages appears even more clearly.

Figure 2:
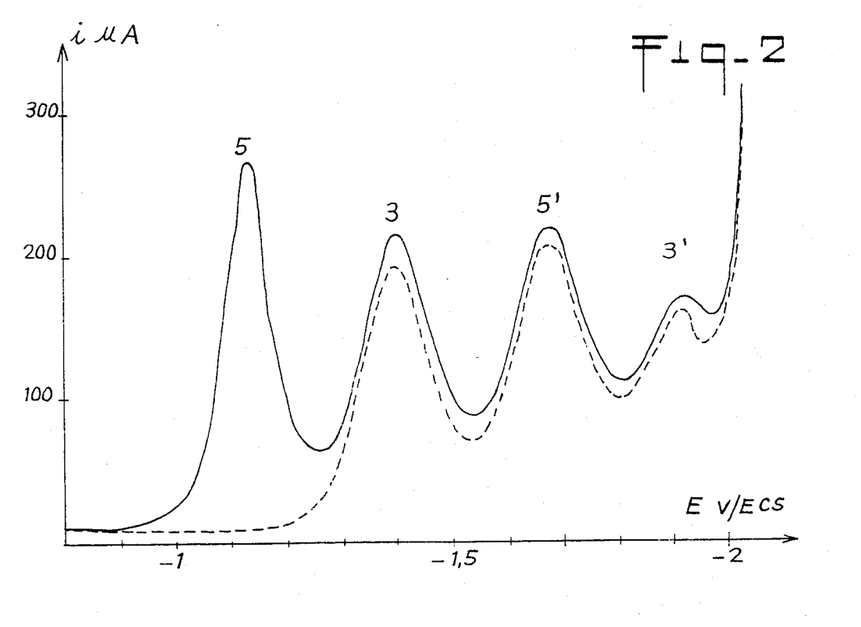
FIG. 2 shows the pulsed polargraph of $T_4$ and $rT_3$ at a concentration of $5.10^{-4}M$ in an aqueous solution containing quatrnary tetramethylammonium hydroxide (0.1M).

FIG. 2 shows the pulsed polarograph of $T_4$ (in solid lines) and of $rT_3$ (in broken lines) at a concentration of $5.10^{-4}M$ in an aqueous solution containing quaternary tetramethylammonium hydroxide (0.1M). This figure shows that the first peak (which corresponds to the first wave of FIG. 1) is that of the reduction of the iodine fixed in 5 position.

Consequently, if a reduction is effected at controlled potential, an iodine in a determined position may be selectively eliminated (at least for the two iodines in 3 or 5 position, for which the potentials are notably different).

The values of the potentials at which operation must be carried out to obtain a selective reduction, may vary slightly (about ±0.2 v) with the concentration of the raw material to be reduced, and with the concentration of the quaternary ammonium hydroxide added to the electrolytic solution. These values are thus determind by plotting the polarograph of the substance to be reduced in the operational conditions chosen, and in the presence of 8 per 10,000 parts of gelatin in order to eliminate the polarographic maxima.

Electrochemical reduction in the range of potentials located in the upper part of the polarographic wave is then effected.

By reducing the thyroxine under the conditions in which the polarograph of FIG. 1 was plotted (concentration of the raw material $5.10^{-4}M$ in tetramethylammonium hydroxide 0.1M) at controlled potential of −1.15 v, $rT_3$ is exclusively obtained (without reducing the iodines in 3,3' and 5' position).

3',5'-diiodothyronine ($T'_2$) may also be obtained by reducing the thyroxine at −1.30 v. Similarly, reduction of the 3,3',5-triiodothyronine ($T_3$) at 1.20 v will lead to 3,3'-diiodothyronine ($rT_2$).

The process of selective reduction according to the invention may therefore be used for syntheses other than those of $rT_3$ and in particular for preparing $T'_1$ by reduction of $T_3$ or of $rT'_2$ at about −1.40 v, or for preparing $T_1$ by reduction of $T_2$ at about −1.20 v, or for preparing $T'_2$ by reduction of $rT_3$ at about 1.5 V.

The process of selective reduction according to the invention may be used for all the thyronines mentioned, whether or not they contain one or more constituent atoms (iodine, carbon, nitrogen, hydrogen or oxygen) in their form of natural or stable or radioactive isotopes.

The process according to the invention may also be applied to the synthesis of iodothyroacetic acids whose structures are very similar to those of the iodothyronines (cf. Tables I and II).

Figure 5:
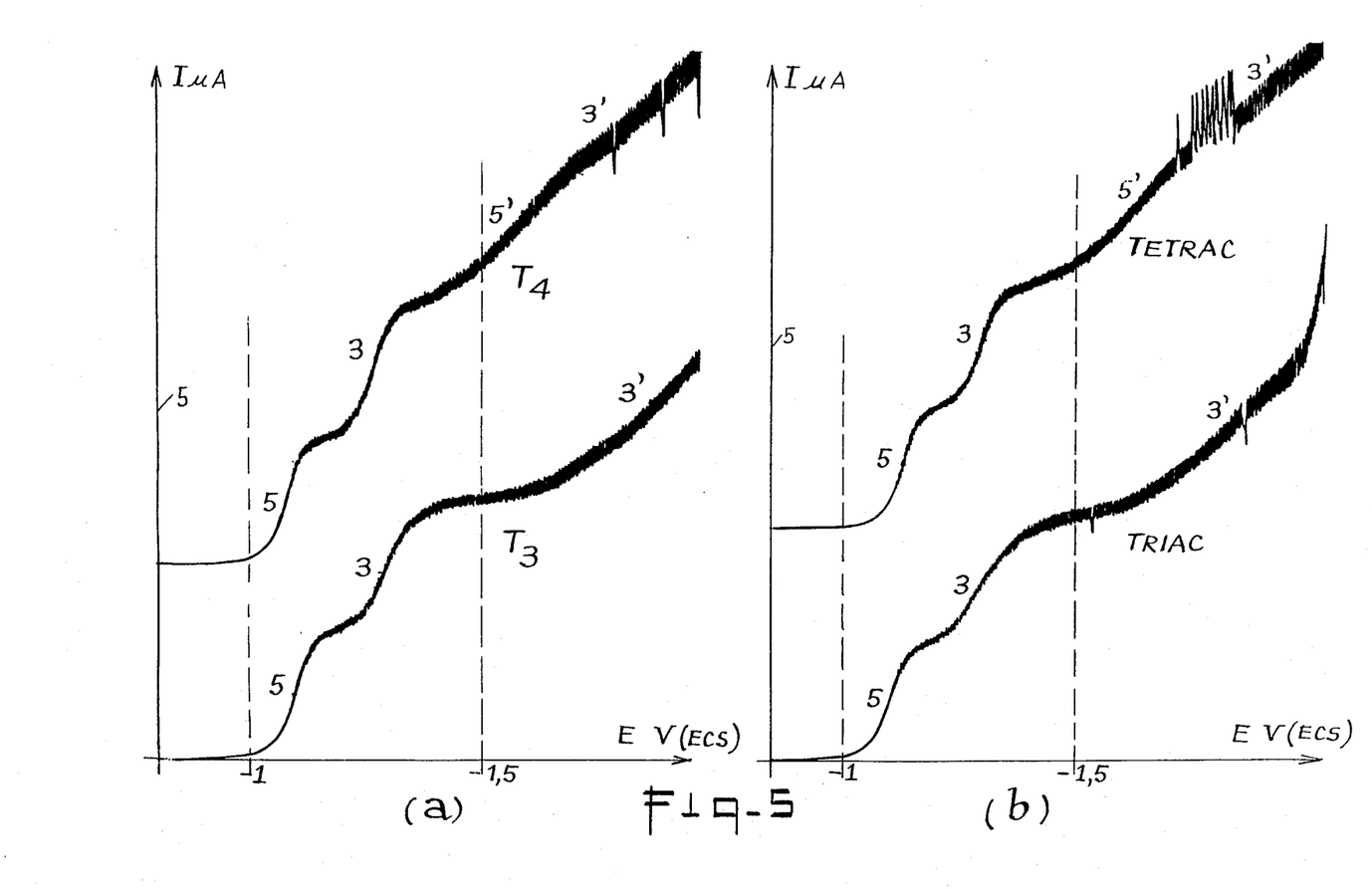
FIG. 5 shows the compared polarographs of the two iodothyronines $T_4$ and $T_3$ (FIG. 5a) and two corresponding iodothyroacetic acids (TETRAC and TRIAC) (FIG. 5b).

FIG. 5 shows the compared polarographs of the two iodothyronines $T_4$ and $T_3$ (FIG. 5a) and two corresponding iodothyroacetic acids (TETRAC and TRIAC) (FIG. 5b) at a concentration of $5.10^{-4}M$ in a 0.1M tetramethylammonium hydroxide medium. It is observed that, for the two types of structures, differing only by the $-NH_2$ group and by the condensation in carbon, the reduction of the iodines in 3 and 5 position is produced virtually at the same potentials. In the same way as the reductions of $T_4$ and of $T_3$ at about −1.20 V lead respectively of $rT_3$ and to the 3,3'—$T_2$ or $rT_2$, similarly the reductions of TETRAC and of TRIAC at about 1.20 V will respectively lead to the rTRIAC and to the 3,3' DIAC.

Such a deiodization by stages presents, with respect to the chemical reduction by hydrogen in the presence of Raney nickel, the advantage of a considerable selectivity. By operating at a controlled potential, one is certain to reduce one sole iodine in determined position, and thus to obtain a very pure product, this with an almost quantitative yield.

EXAMPLE OF PREPARATION OF $rT_3$ BY REDUCTION AT CONTROLLED POTENTIAL

The reduction is effected in an electrochemical cell with mercury cathode described by (MOINET C. and PELTIER D.—Bull. Soc. Chim. (France), 1969, 690) associated with a potentiostat manufactured by SOLEA-TACUSSEL (Type PRT 20-2). The fritted glass separating the anode and cathode compartments is provided with an agar-agar gel prepared in a saturated tetramethylammonium perchlorate medium in order to avoid diffusion of the anode and cathode products. The saturated calomel reference electrode is provided with a tetramethylammonium chloride extension. The anode is constituted by a winding of platinum immersed in a 0.1M tetramethylammonium perchlorate solution. Several tests were made under the following conditions:

130 cm$^3$ of L-thyroxine (made by the firm SIGMA) at the concentration of 2.5. $10^{-3}M$ in 0.1M tetramethylammonium hydroxide are introduced into the cell. A polarograph is firstly plotted to determine the exact maximum potential at which only the iodine 5 of the thyroxine is reduced: viz. −1.20 v with respect to the reference electrode described above. Electrolysis is then effected until the electrolysis current recorded reaches a constant, virtually zero value, with the exception of the residual current, which represents about 5½ hours. After having removed electrodes and diaphragm, the solution is filtered then taken to pH=6.5 (using pH-meter) by the addition of an approximately 1N hydrochloric acid solution. The compound $rT_3$ precipitates immediately; after heating for a few minutes at 50° C. to promote flocculation, filtering is effected over fritted glass of No. 4 porosity, or centrifugation is effected. After several washes in distilled water (up to the disappearance of the chloride ions with silver nitrate), the white product is dried in the desiccator over silica-gel. Yield was quantitative for the three tests carried out: 200 mg.

IDENTIFICATION OF THE COMPOUND PREPARED

The nature of the compound $rT_3$ was checked by the following different methods by comparison with a standard commercial sample (HENNING Berlin GmbH):
NMR check in deuterium DMSO medium
direct and pulsed polarography chromatography on paper
radioimmunological dosage
dosage of the total iodine
microanalysis All these controls leave no doubt as to the nature of the compound obtained which is identical in all points to the commercial standard.

DETERMINATION OF THE PURITY OF rT₃

The electrochemical reduction at controlled potential is translated by an exponential reduction of the electrolysis current as a function of time. If the reduction is not continued for a sufficient period of time, there may still remain some non-reduced product, T₄ in the present case.

There again, the electrochemical technique of pulsed polarography enables the disappearance of the reagent to be monitored. In fact, with reference to FIG. 2, it will be observed that the thyroxine presents a peak of very substantial reduction at $-1.125$ v for a concentration of $5.10^{-4}$M in 0.1M tetramethylammonium hydroxide medium. Since the presence of this impurity is suspected, it suffices to record the pulsed polarograph of rT₃ to be sure of the absence of a peak at $-1.125$ v: the absence of this peak indicates that the reduction was quantitative.

Figure 3:
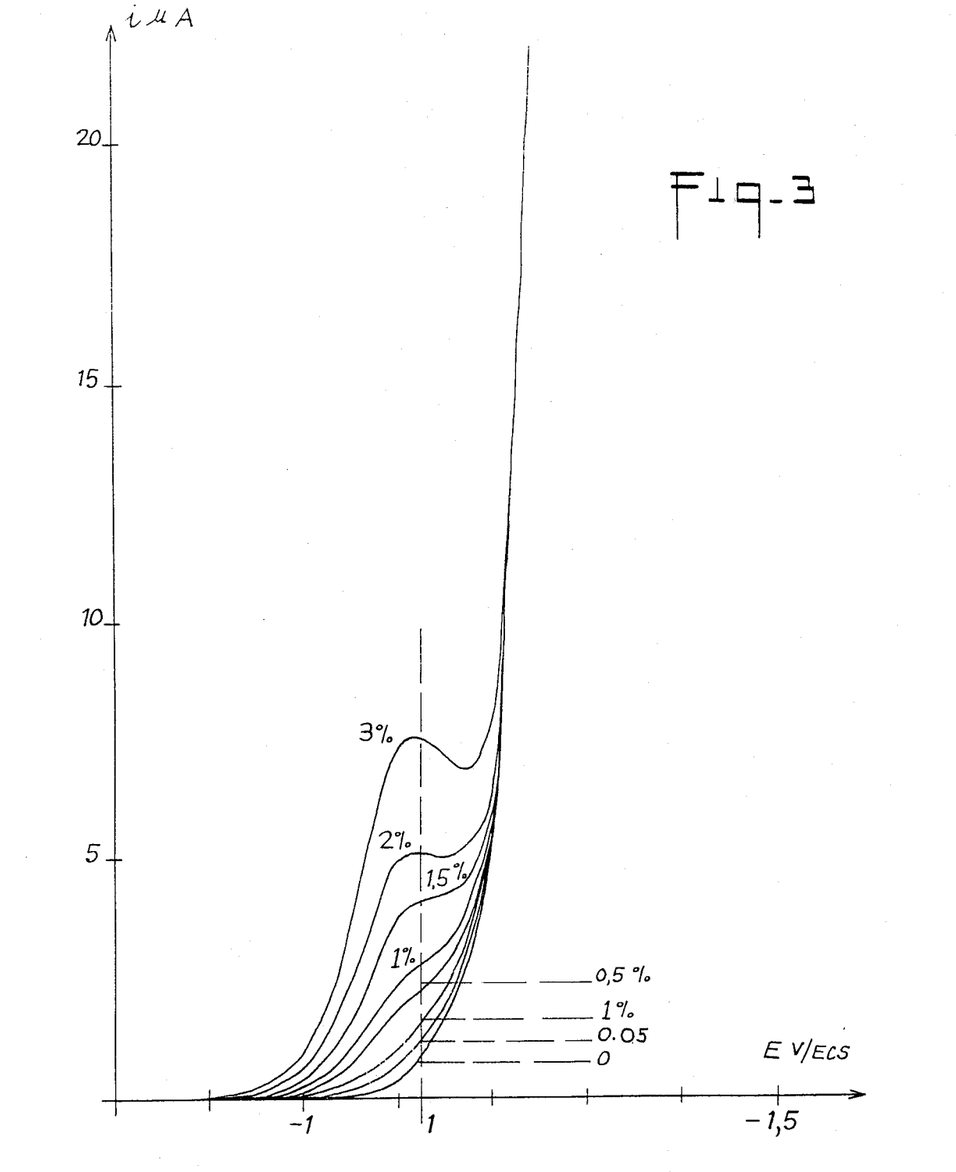
FIG. 3 shows a polarograph of $rT_3$ with $T_4$ added for purity test.

FIG. 3 groups together the polarographs (limited to the relevant range of potential) of rT₃ prepared by the process described hereinabove to which have been added increasing quantities of T₄ in order to test the purity of the compound prepared; it is observed that the peak 5 of T₄ appears very clearly at the base of that of rT₃.

Figure 4:
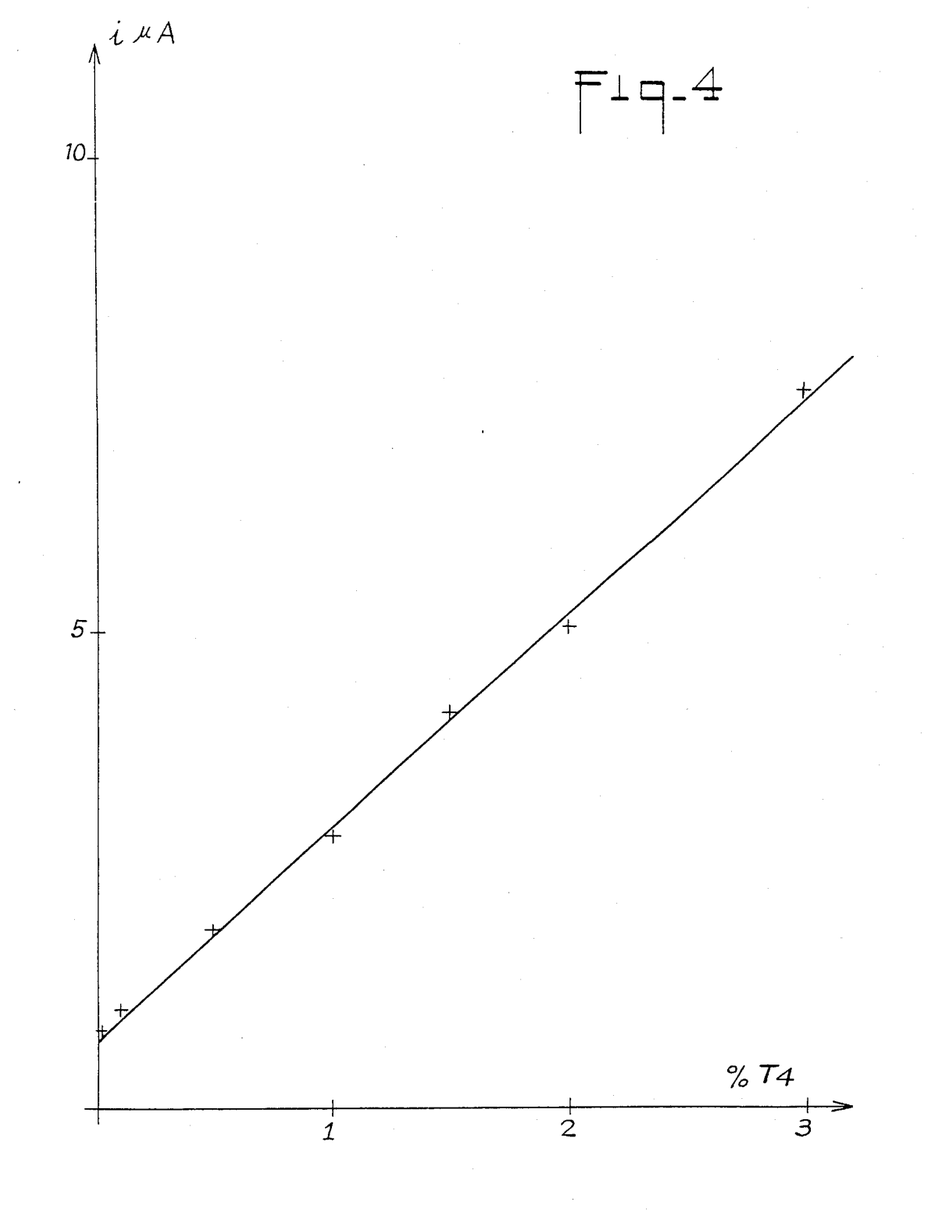
FIG. 4 shows the curve, as a function of percentage of impurity $T_4$ of the heights of the peak (in nA) measured at $-1.125$ V on the polarographs of FIG. 3.

FIG. 4 shows the curve, as a function of the percentage of impurity T₄, of the heights of the peak (in nA) measured at $-1.125$ v on the polarographs of FIG. 3. These heights vary linearly as a function of the content of T₄. If this impurity can really be metered quantitatively up to a content of the order of $1°/_{oo}$, one must be content with an estimation for lower contents: in fact, the peak of T₄ disappears progressively in the base line of rT₃. However, it will be observed that, at a content of $0.5°/_{oo}$, the polarograph differs very substantially from that of rT₃ considered as pure.

EXAMPLE OF PREPARATION OF AN IODOTHYROACETIC ACID: rTRIAC

By electrolysis at $-1.15$ V with respect to calomel, of 20 cm³ of a $4.4.10^{-4}$M solution of TETRAC in a microcell (deriving from that used for the iodothyronines) for 5½ hours, in a 0.1M tetramethylammonium hydroxide medium, a limpid solution is obtained which, acidified by a 10% acetic acid solution, allows a white precipitate to deposit. After centrifugation, washing with water and drying overnight in a desiccator employing P₂O₅, more than 40 mg of rTRIAC are collected, which corresponds to a yield greater than 70%.

FIG. 6 shows the polarographs:
(a) of the reduction product obtained and
(b) of the TETRAC, at a concentration of $5.10^{-4}$M in a 0.1M tetramethylammonium hydroxide medium.

By polarographic analysis, the total absence of iodine in 5 position is therefore verified without ambiguity according to this Figure, which confirms that the product obtained is indeed rTRIAC. No comparison is possible further to the absence of reference product of commercial source.

In conclusion, the electrochemical reduction at controlled potential of various iodothyronines and iodothyroacetic acids makes it possible to prepare a whole range of interesting compounds. The great merit of electrochemical synthesis is in its high selectivity and its "clean" execution with respect to the reagents. Applied to the reduction of thyroxine, the rT₃ whose price was up to now very high, is obtained quantitatively, in an excellent state of purity;

this reduction tested in a conventional laboratory cell may be extended to a larger scale: it suffices to increase the dimensions of said cell;

finally, the systematic use of the pulsed polarography leads to a precise dosage of very small quantities of T₄ in the rT₃ enabling the purity of the prepared compound to be verified.

TABLE I

TABLE I-continued

T₁

T'₁

TABLE II

TETRAC r TRIAC

TRIAC 3,5 DIAC 3,3' DIAC

3',5' DIAC

TABLE II-continued

3 MIAC

3' MIAC

What is claimed is:

1. A process for preparing triidothyronines, diiodothyronines and monoiodothyronines and triiodothyroacetic acids, diiodothyroacetic acids and monoiodothyroacetic acids containing no iodine in 5-position and/or in 3-position consisting essentially of the steps of forming an electrolyte consisting of an alkaline aqueous solution of a material selected from the class consisting of sodium hydroxide and tetraalkylammonium hydroxide, adding a material selected from the group consisting of thyroxine, triiodothyronine, diiodothyronine, tetraiodothyroacetic acid triiodothyroacetic acid or diiodothyroacetic acid containing iodine in 5-position and/or in 3-position to said solution, subjecting the resulting solution to selective electrochemical reduction at controlled potential of reduction, with respect to an electrode of reference, to effectively eliminate iodine in 5-position and/or iodine in 3-position.

2. The process of claim 1 wherein the potential at which the reduction is carried out is previously determined by plotting a polarogram of the material of said group to be reduced with an electrolyte of said class which will serve for reduction, said polarogram plotting the intensity versus the potential of reduction, and by noting the range of potentials of reduction located in the upper part of the polarographic wave corresponding to the selective elimination of iodine in 5-position and/or in 3-position.

3. The process of claim 1 wherein the material of said group to be reduced in said aqueous solution is present at a concentration of $5.10^{-4}M$, said material of said class is 0.1M tetramethylammonium hydroxide and the electrode of reference is a saturated calomel electrode.

4. The process of one of claims 1 or 2 wherein thyroxine to be reduced is present at a concentration of $2.5 \times 10^{-3}M$ in 0.1M tetramethylammonium hydroxide aqueous solution, said electrochemical reduction is effected at a maximum potential of $-1.20$ volts with respect to a saturated calomel electrode of reference.

5. The process of claim 4 wherein fritted glass divides said electrochemical cell into anode and cathode compartments and wherein an agaragar gel is present in said fritted glass, said agar-agar gel being prepared in a saturated tetramethylammonium perchlorate medium.

6. The process of claim 4 wherein said electrochemical reduction of said solution of thyroxine is continued until the electrolysis current reaches a constant virtually zero intensity with the exception of the residual current; filtering the electrolytic solution, adding a hydrochloric acid solution to bring said electrolytic solution to pH 6.5, heating said electrolytic solution to 50° C. to promote flocculation of the precipate of 3,3'5'-triiodothyronine, and collecting the same by filtration or centrifugation.

7. The process of claim 3 wherein thyroxine of said group is subjected to said electrochemical reduction at a potential of −1.15 volts to prepare 3,3',5'-triiodothyronine.

8. The process of claim 3 wherein thyroxine of said group is subjected to said electrochemical reduction at a potential of −1.30 volts to prepare 3',5'-diiodothyronine.

9. The process of claim 3 wherein 3,3',5-triiodothyronine of said group is subjected to said electrochemical reduction at a potential of −1.20 volts to prepare 3,3'-diiodothyronine.

10. The process of claim 3 wherein 3,3',5-triiodothyronine of said group is subjected to said electrochemical reduction at a potential of −1.40 volts to prepare 3'-monoiodothyronine.

11. The process of claim 3 wherein 3,3',5'-triiodothyronine of said group is subjected to said electrochemical reduction at a potential of −1.5 volts to prepare 3',5'-diiodothyronine.

12. The process of claim 3 wherein 3,3'-diiodothyronine is subjected to said electrochemical reduction at a potential of −1.40 volts to prepare 3'-monoiodothyronine.

13. The process of claim 3 wherein 3,5-diiodothyronine is subjected to said electrochemical reduction at a potential of −1.2 volts to prepare 3-monoiodothyronine.

14. The process of claim 3 wherein 3,3',5,5'-tetraiodothyroacetic acid is subjected to said electrochemical reduction at a potential of −1.2 volts to prepare 3,3',5'-triiodothyroacetic acid.

15. The process of claim 3 wherein 3,3',5-triiodothyroacetic acid is subjected to said electrochemical reduction at a potential of −1.2 volts to prepare 3,3'-diiodothyroacetic acid.

16. The process of claim 3 wherein said reduction is effected in an electrochemical cell with a cathode of mercury, an anode of platinum and a saturated calomel electrode of reference and wherein a potentiostat is in circuit with said cathode.

* * * * *